US006403074B1

(12) United States Patent
Blankenburg et al.

(10) Patent No.: US 6,403,074 B1
(45) Date of Patent: Jun. 11, 2002

(54) USE OF POLYMERS CONTAINING POLYSILOXANE FOR COSMETIC FORMULATIONS

(75) Inventors: Rainer Blankenburg, Stuttgart-Feuerbach; Reinhold Dieing, Schifferstadt; Wolfgang Müller; Axel Sanner, both of Frankenthal; Volker Schehlmann, Römerberg; Katrin Zeitz, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,609

(22) PCT Filed: Jul. 20, 1998

(86) PCT No.: PCT/EP98/04482

§ 371 (c)(1),
(2), (4) Date: Jan. 11, 2000

(87) PCT Pub. No.: WO99/04750

PCT Pub. Date: Feb. 4, 1999

(30) Foreign Application Priority Data

Jul. 23, 1997 (DE) .......................................... 197 31 529

(51) Int. Cl.$^7$ .......................... A61K 7/06; A61K 7/075; A61K 7/00
(52) U.S. Cl. ................ 424/70.12; 424/70.1; 424/70.11; 424/47; 510/119
(58) Field of Search .............................. 424/70.1, 70.11, 424/70.12, 47; 510/119

(56) References Cited

U.S. PATENT DOCUMENTS

| 3,471,588 A | | 10/1969 | Kanner |
| 5,480,634 A | | 1/1996 | Hayama et al. |
| 5,565,194 A | | 10/1996 | Burkhart et al. |
| 6,056,945 A | * | 5/2000 | Cauwet-Martin et al. |

FOREIGN PATENT DOCUMENTS

| DE | 1 645 569 | 7/1970 |
| EP | 408 311 | 1/1991 |
| EP | 412 707 | 2/1991 |
| EP | 582 152 | 2/1994 |
| EP | 670 342 | 9/1995 |
| FR | 2 740 037 | 4/1997 |
| WO | 93/23446 | 11/1993 |

* cited by examiner

Primary Examiner—Thurman K. Page
Assistant Examiner—Brian K. Seidleck
(74) Attorney, Agent, or Firm—Keil & Weinkauf

(57) ABSTRACT

Process for preparing polymers which are water-soluble or water-dispersible or which, if consisting of monomers with neutralizable radicals, are soluble in water or dispersible in water in neutralized form, by subjecting (a) ethylenically unsaturated monomers to free-radical polymerization in the presence of (b) polyalkylene oxide-containing silicone derivatives.

7 Claims, No Drawings

USE OF POLYMERS CONTAINING POLYSILOXANE FOR COSMETIC FORMULATIONS

This application is a 371 of PCT/EP98/04482, filed Jul. 20, 1998.

Synthetic polymers have been employed successfully for the setting of hair styles for almost 50 years. Whereas to start with vinyl lactam homopolymers and copolymers were preferably employed, polymers containing carboxylate groups gained in importance later on. The desired profile of properties, such as firm setting at high atmospheric humidity, elasticity, ease of wash-off from the hair, and compatibility with the other formulation components, is achieved by copolymerizing a combination of hydrophobic, elasticizing and carboxyl-containing monomers.

Although these requirements are nowadays met by a variety of polymer types, more and more frequently the feel of the hairstyles set with these polymers is perceived as being unpleasantly dull and unnatural. Attempts to improve formulations by means of additives have not to date led to entirely satisfactory results: the addition of customary plasticizers, although improving the feel, at the same time reduces the setting effect in many cases. The polysiloxanes frequently employed are incompatible with the polar polymers and often require further additives to allow them to be formulated at all. Separation can lead to problems both during storage of the formulation and during its use.

There has therefore been no lack of attempts to bind polysiloxane groups covalently to the hairsetting polymer in order to prevent separation. For example, European Patent Application EP 0 408 311 describes haircare polymers formed from a monomer which contains polysiloxane groups and from customary hydrophilic and hydrophobic monomers. European Patent Applications EP 0 412 704 to EP 0 412 707 propose polymerizing polysiloxane groups, in the form of macromonomers with molar masses from 1000 to 50,000, with customary hydrophobic and hydrophilic monomers. The synthesis of these monomers is extremely laborious. It is difficult to separate unreacted macromonomers and their unreactive impurities from the polymers, owing to their high molecular weight. They constitute a toxicological and allergenic risk. Moreover, the resulting copolymers can often only achieve a good effect by being formulated in combination with further polymers, carriers and other auxiliaries, as detailed in the abovementioned specifications.

DE 42 40 108 describes polysiloxane-containing binders suitable as dirt-repelling coatings, especially as antigraffiti coatings. However, these binders are paintlike and are not suitable for cosmetic purposes.

DE 16 45 569 describes a process for preparing organosilicone graft copolymers and their use as foam compositions.

It is an object of the present invention to provide polymers for hair cosmetology which do not have the disadvantages set out above.

We have found that this object is achieved by the use of polymers which are water-soluble or water-dispersible or which, if consisting of monomers with neutralizable radicals, are soluble in water or dispersible in water in neutralized form, which are obtainable by subjecting (a) ethylenically unsaturated monomers to free-radical polymerization in the presence of (b) polyalkylene oxide-containing silicone derivatives, for cosmetic formulations.

By "water-dispersible" in the context of the invention are meant polymers which in contact with water within 24 hours form a fluid in which no solid particles can be made out with the naked eye. To test whether a polymer is water-dispersible, 100 mg of the polymer in the form of a film 100 µm thick are placed in 100 ml of water (20° C.) and shaken on a commercially customary shaking table for 24 hours. If solid particles can no longer be perceived after the shaking, but the fluid possesses turbidity, the polymer is water-dispersible; in the absence of turbidity, it is referred to as water-soluble.

If the silicone compounds are not present during polymerization but instead are mixed in after polymerization, then the result is usually very soft, tacky films unsuitable for the applications in hair cosmetology in accordance with the invention (see Comparative Examples 8 and 24).

This is evident by the fact that grafting of the polymers onto the silicone compounds may possibly occur during polymerization, and that this contributes to the good film properties such as freedom from tack, high surface smoothness, and hardness.

However, it is also possible to conceive mechanisms other than grafting by which the novel polymers arrive at their advantageous properties.

As suitable polymerizable monomers (a) it is possible to use, preferably, ethylenically unsaturated monomers. In this context use can be made of either a single monomer or of combinations of two or more monomers. By polymerizable is meant that the monomers used can be polymerized using any conventional synthetic method.

Such a method can, for example, be solution, emulsion, inverse emulsion, suspension, inverse suspension or precipitation polymerization, without the methods which can be used being restricted to these. In the case of solution polymerization, the solvent used can be water, customary organic solvents, or the novel silicone derivatives themselves.

Monomers which can be polymerized in a reaction which is initiated by free radicals are preferred. The term ethylenically unsaturated means that the monomers possess at least one polymerizable carbon-carbon double bond, which may be in mono-, di-, tri- or tetra-substituted form.

The monomers (a) of the polysiloxane-comprising polymers of the present invention can account for from 50 to 99.9% by weight, preferably from 70 to 99% by weight and, with particular preference, from 85 to 98% by weight.

The preferred ethylenically unsaturated monomers (a) can be described by the following formula:

where

X is selected from the group consisting of —OH, —OM, —OR$^8$, NH$_2$, —NHR$^8$, N(R$^8$)$_2$;

M is a cation selected from the group consisting of: Na$^+$, K$^+$, Mg$^{++}$, Ca$^{++}$, Zn$^{++}$, NH$_4^+$, alkylammonium, dialkylammonium, trialkylammonium and tetraalkylammonium;

the radicals R$^8$ can be identical or different and can be selected from the group consisting of —H, C1–C40 linear- or branched-chain alkyls, N,N-dimethylaminoethyl, 2-hydroxyethyl, 2-methoxyethyl, 2-ethoxyethyl, hydroxypropyl, methoxypropyl and ethoxypropyl;

R$^7$ and R$^6$ are selected independently of one another from the group consisting of: —H, C$_1$–C$_8$ linear- or branched-chain alkyls, methoxy, ethoxy, 2-hydroxyethoxy, 2-methoxyethoxy and 2-ethoxyethyl.

Representative, but nonlimiting, examples of suitable monomers (a) are acrylic acid and its salts, esters and amides. The salts can be derived from any desired nontoxic metal, ammonium or substituted ammonium counterions.

The esters can be derived from C$_1$–C$_{40}$ linear, C$_3$–C$_{40}$ branched-chain or C$_3$–C$_{40}$ carbocyclic alcohols, from polyfunctional alcohols having 2 to about 8 hydroxyls, such as ethylene glycol, hexylene glycol, glycerol and 1,2,6-hexanetriol, from amino alcohols or from alcohol ethers, such as methoxyethanol and ethoxyethanol or polyethylene glycols.

Also suitable are N,N-dialkylaminoalkyl acrylates and methacrylates and N-dialkylaminoalkylacryl- and -methacrylamides of the formula (II)

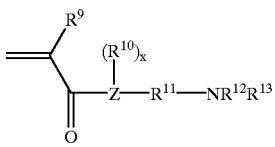

(II)

where $R^9$=H, alkyl of 1 to 8 carbons, $R^{10}$=H, methyl, $R^{11}$=alkylene of 1 to 24 carbons, optionally substituted by alkyl, $R^{12}$, $R^{13}$=$C_1$–$C_{40}$ alkyl, Z=nitrogen if x=1 or oxygen if x=0.

The amides can be unsubstituted, N-alkyl- or N-alkylamino-monosubstituted or N,N-dialkyl-substituted or N,N-dialkylamino-disubstituted, the alkyls or alkylaminos being derived from C1–C40 linear, C3–C40 branched-chain or C3–C40 carbocyclic units. In addition, the alkylaminos can be quaternized.

Preferred monomers of the formula II are N,N-dimethylaminomethyl, N,N-diethylaminomethyl, N,N-dimethylaminoethyl and N,N-diethylaminoethyl (meth) acrylates.

Monomers (a) which can likewise be used are substituted acrylic acids and salts, esters and amides thereof, the substituents in the carbons being in the two or three position of the acrylic acid and being selected independently of one another from the group consisting of C1–C4 alkyl, —CN and COOH. Particular preference is given to methacrylic, ethacrylic and 3-cyanoacrylic acids. The salts, esters and amides of these substituted acrylic acids can be selected as described above for the salts, esters and amides of acrylic acid.

Other suitable monomers (a) are vinyl esters and allyl esters of

C1–C40 linear, C3–C40 branched-chain or C3–C40 carbocyclic carboxylic acids (examples: vinyl acetate, propionate, neononanoate, neoundecanoate or t-butylbenzoate); vinyl or allyl halides, preferably vinyl chloride and allyl chloride, vinyl ethers, preferably methyl, ethyl, butyl or dodecyl vinyl ether, vinylformamide, vinylmethylacetamide, vinylamine; vinyllactams, preferably vinylpyrrolidone and vinylcaprolactam, and vinyl- or allyl-substituted heterocyclic compounds, preferably vinylpyridine, vinyloxazoline and allylpyridine.

Also suitable are N-vinylimidazoles of the formula III, where $R^{14}$ to $R^{16}$ independently of one another are hydrogen, C1–$C_4$-alkyl or phenyl:

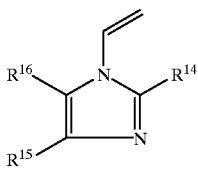

(III)

Further suitable monomers (a) are diallylamines of the formula (IV)

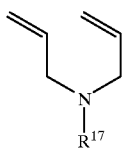

(IV)

where $R^{17}$=C1 to C24 alkyl.

Other suitable monomers (a) are vinylidene chloride; and hydrocarbons with at least one carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene and mixtures of these monomers.

Particularly suitable monomers (a) are acrylic, methacrylic and ethylacrylic acid, methyl, ethyl, propyl, n-butyl, isobutyl, t-butyl, 2-ethylhexyl and decyl acrylate, methyl, ethyl, propyl, n-butyl, isobutyl, t-butyl, 2-ethylhexyl and decyl methacrylate, methyl, ethyl, n-butyl, isobutyl, t-butyl, 2-ethylhexyl and decyl ethacrylate, 2,3-dihydroxypropyl acrylate, 2,3-dihydroxypropyl methacrylate, 2-hydroxyethyl acrylate, hydroxypropyl acrylate, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth)acrylates, unsaturated sulfonic acids, such as acrylamidopropanesulfonic acid, for example; acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylimidazole, N,N-dimethylaminomethyl (meth) acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino) butyl]methacrylamide, N-[8-(dimethylamino)octyl] methacrylamide, N-[12-(dimethylamino)dodecyl] methacrylamide, N-[3-(diethylamino)propyl] methacrylamide, N-[3-(diethylamino)propyl]acrylamide; maleic acid, fumaric acid, maleic anhydride and its monoesters, crotonic acid, itaconic acid, diallyldimethylammonium chloride, vinyl ethers (for example, methyl, ethyl, butyl or dodecyl vinyl ether), vinylformamide, vinylmethylacetamide, vinylamine; methyl vinyl ketone, maleimide, vinylpyridine, vinylimidazole, vinylfuran, styrene, styrene sulfonate, allyl alcohol and mixtures thereof.

Of these, particular preference is given to acrylic, methacrylic, maleic, fumaric and crotonic acid, maleic anhydride and its monoesters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, N-t-butylacrylamide, N-octylacrylamide, 2-hydroxyethyl acrylate, hydroxypropyl acrylate, 2-hydroxyethyl methacrylate, hydroxypropyl methacrylate, alkylene glycol(meth)-acrylates, unsaturated sulfonic acids, such as acrylamidopropanesulfonic acid, for example, vinylpyrrolidone, vinylcaprolactam, vinyl ethers (for example, methyl, ethyl, butyl or dodecyl vinyl ether), vinylformamide, vinylmethylacetamide, vinylamine, 1-vinylimidazole, 1-vinyl-2-methylimidazole, N,N-dimethylaminomethyl methacrylate and N-[3-(dimethylamino)propyl]methacrylamide; 3-methyl-1-vinylimidazolium chloride, 3-methyl-1-vinylimidazolium methylsulfate, N,N-dimethylaminoethyl methacrylate, N-[3-(dimethylamino)propyl]methacrylamide quaternized with methyl chloride, methyl sulfate or diethyl sulfate.

Monomers having a basic nitrogen can be quaternized as follows:
the amines are suitably quaternized using, for example, alkyl halides of 1 to 24 carbon atoms in the alkyl, examples being methyl chloride, methyl bromide, methyl iodide, ethyl chloride, ethyl bromide, propyl chloride, hexyl chloride, dodecyl chloride, lauryl chloride and benzyl halides, especially benzyl chloride and benzyl bromide. Further suitable quaternizing agents are dialkyl sulfates, especially dimethyl sulfate or diethyl sulfate. The basic amine can also be quaternized with alkylene oxides, such as ethylene oxide or propylene oxide, in the presence of acids. Preferred quaternizing agents are methyl chloride, dimethyl sulfate and diethyl sulfate.

Quaternization can be carried out before or after polymerization.

In addition, it is also possible to employ the reaction products of unsaturated acids, such as acrylic or methacrylic acid, with a quaternized epichlorohydrin of the formula (V) ($R^{18}$=C1 to C40 alkyl).

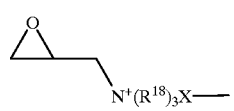

(V)

Examples of such products are: (meth) acryloyloxyhydroxypropyltrimethylamonium chloride and (meth) acryloyloxyhydroxypropyltrimethylamonium chloride.

The basic monomers can also be cationized by neutralizing them with mineral acids, such as sulfuric, hydrochloric, hydrobromic, hydroiodic, phosphoric or nitric acid, or with organic acids, such as formic, acetic, lactic or citric acid.

Monomers (a) which can be employed include, in addition to the abovementioned monomers, macromonomers such as, for example, silicone-containing macromonomers having one or more free-radically polymerizable groups, or alkyloxazoline macromonomers, as are described, for example, in EP 408 311.

It is also possible to employ fluorine-containing monomers as described, for example, in EP 558 423; compounds with a crosslinking action, or molecular weight regulators, in combination or singly.

Regulators possible for use are the conventional compounds known to the skilled worker, such as sulfur compounds (mercaptoethanol, 2-ethylhexyl thioglycolate, thioglycolic acid or dodecyl mercaptan for example) and also tribromochloromethane or other compounds which act to regulate the molecular weight of the resulting polymers.

If desired it is also possible to employ silicone compounds which contain thiol groups.

The use of silicone-free regulators is preferred.

Crosslinking monomers which can be employed are compounds having at least two ethylenically unsaturated double bonds, examples being esters of ethylenically unsaturated carboxylic acids, such as acrylic or methacrylic acid, with polyhydric alcohols, and ethers of at least dihydric alcohols, such as vinyl ethers or allyl ethers. Also suitable are straight-chain or branched, linear or cyclic, aliphatic or aromatic hydrocarbons having at least two double bonds which, in the case of the aliphatic hydrocarbons, must not be conjugated. Further suitable compounds include amides of acrylic and methacrylic acid and N-allylamines of at least difunctional amines such as 1,2-diaminoethane and 1,3-diaminopropane. Triallylamine or corresponding ammonium salts, N-vinyl compounds of urea derivatives, at least difunctional amides, cyanurates or urethanes are also suitable. Further suitable crosslinkers are divinyldioxane, tetraallylsilane and tetravinylsilane.

Examples of particularly preferred crosslinkers are methylenebisacrylamide, triallylamine and triallylammonium salts, divinylimidazole, N,N'-divinylethyleneurea, reaction products of polyhydric alcohols with acrylic or methacrylic acid, methacrylic esters and acrylic esters of polyalkylene oxides or polyhydric alcohols which have been reacted with ethylene oxide and/or propylene oxide and/or epichlorohydrin.

In the polymerization of the monomers (a) it is also possible if desired for other polymers to be present, for example polyamides, polyurethanes, polyesters and homo- and copolymers of ethylenically unsaturated monomers. Examples of such polymers, in some cases also employed in cosmetology, are the polymers known by the tradenames Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastma AQ™.

Polymers like these or others can also be mixed in with the novel polymer preparations after polymerization has taken place.

The novel monomers (a), in so far as they contain ionizable groups, can be neutralized with acids or bases before or after polymerization, in full or in part, in order, for example, to adjust the solubility or dispersibility in water to a desired level.

Examples of suitable neutralizing agents for monomers which carry acid groups are mineral bases, such as sodium carbonate, alkali metal hydroxide and ammonia, organic bases, such as amino alcohols, especially 2-amino-2-methyl-1-propanol, monoethanolamine, diethanolamine, triethanolamine, triisopropanolamine, tris[(2-hydroxy)-1-propyl]amine, 2-amino-2-methyl-1,3-propanediol, 2-amino-2-hydroxymethyl-1,3-propanediol, and diamines, for example lysine.

Possible neutralizing agents for monomers which carry cationizable groups that can be used are, for example, mineral acids, such as hydrochloric, sulfuric or phosphoric acid, and organic acids, such as carboxylic, lactic, citric or other acids.

It is also possible for auxiliaries such as plasticizers, film-forming auxiliaries, pigments, perfumes or others, alone or in combination, to be present in the course of polymerization and/or to be added after polymerization.

When the novel polymers are used in hair cosmetology, especially when used as hairsetting agents, it is advantageous to adjust the glass transition temperature of the polymers to more than 20° C. by means of a suitable combination of ethylenically unsaturated monomers.

Suitable silicone derivatives (b) are the compounds known under the INCI name dimethicone copolyols or silicone surfactants, such as those obtainable under the brand names Abil® (T. Goldschmidt), Alkasil® (Rhône-Poulenc), silicone Polyol Copolymer® (Genesee), Belsil® (Wacker), Silwet® (Witco, Greenwich, Conn., USA) or Dow Corning 190™ (Dow Corning). They include compounds having the CAS Numbers 64365-23-7; 68937-54-2; 68938-54-5; 68937-55-3.

Particularly suitable monomers (b) are those comprising the following structural units:

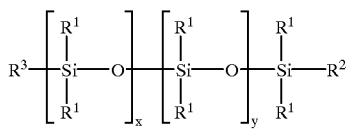
(I)

where:

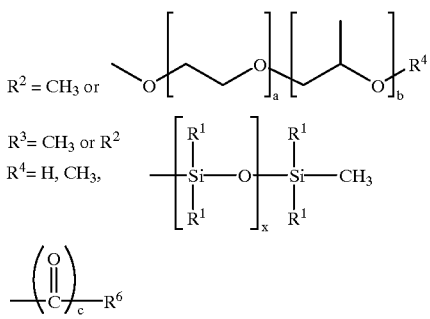

$R^6$ is an organic radical of 1 to 40 carbons which may contain amino, carboxyl or sulfonate groups, or, if c=0, is the anion of an inorganic acid,
and where the radicals $R^1$ can be identical or different and alternatively derive from the group of aliphatic hydrocarbons of 1 to 20 carbons, are cyclic aliphatic hydrocarbons of 3 to 20 carbons, are aromatic in nature or are $R^5$, where:

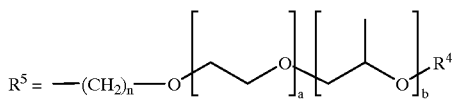

with the proviso that at least one of the radicals $R^1$, $R^2$ or $R^3$ is a polyalkylene oxide-containing radical as defined above, and n is an integer from 1 to 6, x and y are integers such that the molecular weight of the polysiloxane block is from 300 to 30,000,
a,b can be integers from 0 to 50 with the proviso that the sum of a and b is greater than 0, and c is 0 or 1.

Preferred radicals $R^2$ and $R^5$ are those where the sum of a+b is from 5 to 30.

$R^1$ is preferably selected from the following groups: methyl, ethyl, propyl, butyl, isobutyl, pentyl, isopentyl, hexyl, octyl, decyl, dodecyl and octadecyl, cycloaliphatic radicals, especially cyclohexyl, aromatic groups, especially phenyl or naphthyl, mixed aromatic-aliphatic radicals, such as benzyl or phenylethyl, and also tolyl and xylyl and $R^5$.

Particularly suitable radicals $R^4$ are those where, for $R^4$=—(CO)$_c$—$R^6$, $R^6$ is any desired alkyl, cycloalkyl or aryl which has 1 to 40 carbons and may bear further ionogenic groups such as $NH_2$, COOH and/or $SO_3H$.

Preferred inorganic radicals $R^6$ for c=0 are phosphate and sulfate.

Particularly preferred silicone derivatives (b) are those of the general structure:

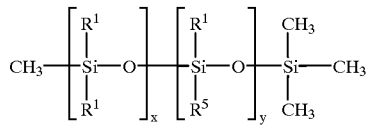

The silicone derivatives (b) are generally present in amounts of 0.1–50, preferably 1–20, and, with particular preference 2–15% by weight in the novel polymer.

Particularly suitable polymers are those which are soluble in water or whose dispersibility in water is such that in a 50:50 (% by volume:% by volume) water/ethanol solvent mixture they are soluble in a proportion of more than 0.1 g/l, preferably more than 0.2 g/l.

Where the polymers consist of monomers which carry neutralizable radicals, preference is given to those polymers which in neutralized form and in a 50:50 (% by volume:% by volume) water/ethanol solvent mixture are soluble in a proportion of more than 0.1 g/l, preferably more than 0.2 g/l.

The novel polymers are suitable for use as active ingredients in cosmetic formulations: both cosmetic skin formulations, such as liquid soap, body lotions, shaving lotions, face lotions, deodorants and other cosmetic lotions, and, in particular, cosmetic hair formulations, such as hair treatments, hair lotions, hair rinses, hair emulsions, treatment fluids for damaged ends, equalizers for permanent waves, hot-oil treatment preparations, conditioners, hairsetting lotions or hairsprays. Depending on the field of use, the cosmetic hair formulations can be applied in the form of a spray, foam, gel, gel spray, lotion or mousse.

The novel mixtures, together with the auxiliaries customary for cosmetic preparations, such as perfume oils, emulsifiers, preservatives, care substances such as panthenol, collagen, vitamins, protein hydrolyzates, stabilizers, pH regulators, colorants, solvents, propellants and other customary additives, can be processed to form gels, sprays, lotions or mousses.

EXAMPLES

The silicone surfactants Wacker Belsil™ DMC 6031 and 6032 used in the examples are obtainable from Wacker Chemie GmbH, Munich, Germany and have the following general structure:

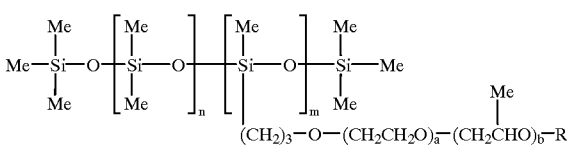

where R=H, —CO—CH$_3$

The silicone surfactants Silwet™ 7600, 7604 and 7605 are obtainable from Witco Corporation, Greenwich, Conn., USA and have the following general structure:

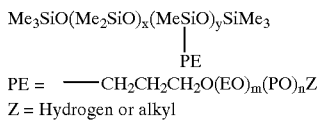

Z = Hydrogen or alkyl

The silicone surfactant Dow Corning 190 Surfactant™ is obtainable from Dow Corning Corporation, Midland, Mich., USA.

Further silicone derivatives (b) can be prepared by processes familiar to the skilled worker as are described, for example, in EP 775 717.

Examples 1–7

To a stirred initial charge there are added, dropwise, 50 g of feedstream 1 and 3.75 g of feedstream 2. The mixture is then heated to 78° C. Subsequently, the remainder of feedstream 1 and of feedstream 2 is added dropwise over the course of 1.5 h. The mixture is stirred for a further 2 h. Then feedstream 3 is added dropwise over the course of 15 minutes and the mixture is stirred at 78° C. for 3 h more.

Examples 1

Initial charge: 175 g of ethanol, 7.5 g of Dow Corning 190™

Feedstream 1: 251 g of t-butyl acrylate, 86 g of methacrylic acid, 37 g of ethyl acrylate, 75 g of ethanol Feedstream 2: 2 g of t-butyl perpivalate, 100 g of ethanol Feedstream 3: 1.5 g of t-butyl perpivalate, 57 g of ethanol Example 2

Initial charge: 175 g of ethanol, 18.75 g of Dow Corning 190™

Feedstream 1: 251 g of t-butyl acrylate, 86 g of methacrylic acid, 37 g of ethyl acrylate, 75 g of ethanol Feedstream 2: 2 g of t-butyl perpivalate, 100 g of ethanol Feedstream 3: 1.5 g of t-butyl perpivalate, 57 g of ethanol Example 3

Initial charge: 175 g of ethanol, 37.5 g of Dow Corning 190™

Feedstream 1: 251 g of t-butyl acrylate, 86 g of methacrylic acid, 37 g of ethyl acrylate, 75 g of ethanol Feedstream 2: 2 g of t-butyl perpivalate, 100 g of ethanol Feedstream 3: 1.5 g of t-butyl perpivalate, 57 g of ethanol Example 4

Initial charge: 175 g of ethanol, 18.75 g of Belsil DMC 6031™

Feedstream 1: 251 g of t-butyl acrylate, 86 g of methacrylic acid, 37 g of ethyl acrylate, 75 g of ethanol Feedstream 2: 2 g of t-butyl perpivalate, 100 g of ethanol Feedstream 3: 1.5 g of t-butyl perpivalate, 57 g of ethanol Example 5

Initial charge: 175 g of ethanol, 37.5 g of Belsil DMC 6031™

Feedstream 1: 279 g of t-butyl acrylate, 96 g of methacrylic acid, 75 g of ethanol Feedstream 2: 2 g of t-butyl perpivalate, 100 g of ethanol Feedstream 3: 1.5 g of t-butyl perpivalate, 57 g of ethanol Example 6

Initial charge: 175 g of ethanol, 37.5 g of Belsil DMC 6032™

Feedstream 1: 300 g of t-butyl acrylate, 75 g of methacrylic acid, 75 g of ethanol Feedstream 2: 2 g of t-butyl perpivalate, 100 g of ethanol Feedstream 3: 1.5 g of t-butyl perpivalate, 57 g of ethanol Example 7

Initial charge: 175 g of ethanol

Feedstream 1: 251 g of t-butyl acrylate, 86 g of methacrylic acid, 37 g of ethyl acrylate, 75 g of ethanol Feedstream 2: 2 g of t-butyl perpivalate, 100 g of ethanol Feedstream 3: 1.5 g of t-butyl perpivalate, 57 g of ethanol Example 8

After polymerization, the solution of the polymer from Example 7 is blended with 10% by weight, based on the polymer present, of the silicone derivative Belsil DMC 6032™.

Example 9

40 g of Silwet™ L 7604 and 180 g of water were charged to a stirred apparatus. This initial charge was heated to 60° C. under nitrogen and with stirring, and feedstream 1, consisting of 240 g of N-vinylpyrrolidone, 267 g of 3-methyl-1-vinylimidazolium methyl sulfate solution (45 percent strength) and 0.4 g of mercaptoethanol, and feedstream 2, consisting of 6 g of 2,2'-azobis(2-amidinopropane) dihydrochloride and 70 ml of water, were metered in over the course of 6 hours. The mixture was subsequently stirred at 60° C. for 2 hours and then diluted with 200 g of water, to give a clear, yellowish polymer solution having a solids content of 41.7% and a K value of 39 (1% strength in 0.5 M Nacl).

Example 10

40 g of Silwet™ L 7604 and 300 ml of water were charged to a stirred apparatus. This initial charge was heated to 65° C. under nitrogen and with stirring, and feedstream 1, consisting of 220 g of N-vinylpyrrolidone, 333 g of 3-methyl-1-vinylimidazolium chloride solution (60 percent strength), and feedstream 2, consisting of 6 g of 2,2'-azobis (2-amidinopropane) dihydrochloride and 70 ml of water, were metered in over the course of 6 hours. The mixture was subsequently stirred for 2 hours more and then diluted with 100 g of water, to give a clear, yellowish polymer solution having a solids content of 43.0% and a K value of 44 (1% strength in 0.5 M NaCl).

Example 11

24 g of Silwet™ L 7604 and 200 ml of water were charged to a stirred apparatus. This initial charge was heated to 65° C. under nitrogen and with stirring, and feedstream 1, consisting of 160 g of N-vinylpyrrolidone, 80 g of methacryloyloxyethyl-N-dimethyl-N-ethylammonium ethyl sulfate and 300 g of water, and feedstream 2, consisting of 1.3 g of 2,2'-azobis(2-amidinopropane) dihydrochloride and 100 g of water, were metered in over the course of 6 hours. The mixture was subsequently stirred for 2 hours and then diluted with 300 g of water, to give a clear, yellowish polymer solution having a solids content of 22.4% and a K value of 85 (1% strength in 0.5 M NaCl).

Examples 12 and 13

306 g of N-t-butylacrylamide, 234 g of ethyl acrylate, 60 g of acrylic acid and 60 g of a dimethicone copolyol were suspended in a mixture of 1.4 g of mercaptoethanol and 5.8 g of a polyacrylic acid (obtainable under the designation Sokalan PA 110 S from BASF AG). The resulting suspension is heated to 75° C. and then 1.2 g of t-butyl peroctoate are added. After 30 or 45 minutes, respectively, a further gram in each case of t-butyl peroctoate is added. Further initiator is added after the following times: 1 h: 1 g at 80° C.; 1.5 h: 1 g; 2 h: 1 g at 90° C.; 3 h: 2.7 g; after 4.5 and 6 h in each case 1 g. Then after polymerization is continued for 1 h.

The dimethicone polyols used were:

Example 12: Wacker Belsil DMC 6031

Example 13a: Wacker Belsil DMC 6032

Example 13b: Witco Silwet® L-7500

Example 14

Comparative Example 306 g of N-t-butylacrylamide, 234 g of ethyl acrylate and 60 g of acrylic acid were suspended in a mixture of 1.4 g of mercaptoethanol and 5.8 g of a polyacrylic acid (obtainable under the designation Sokalan PA 110 S from BASF-AG). The resulting suspension is heated to 75° C. and then 1.2 g of t-butyl peroctoate are added. After 30 or 45 minutes, respectively, a further gram in each case of t-butyl peroctoate is added. Further initiator is added after the following times: 1 h: 1 g at 80° C.; 1.5 h: 1 g; 2 h: 1 g at 90° C.; 3 h: 2.7 g; after 4.5 and 6 h in each case 1 g. Then afterpolymerization is continued for 1 h.

Example 15

A mixture of 744 g of water, 0.25 g of sodium lauryl sulfate and 70 g of feedstream 1 is heated to 40° C. Then 16 g of a 7% strength aqueous sodium persulfate solution are added. The mixture is subsequently heated to 80° C., and the remainder of feedstream 1 is metered in over the course of two hours. Then 178 g of water are added and the mixture is afterpolymerized at 80° C. for two hours.
Feedstream 1:

300 g of water 2 g of sodium lauryl sulfate 15.7 g of silicone copolyol (Silwet L7605)

470 g of tert-butyl acrylate 70 g of ethyl acrylate 161 g of methacrylic acid 3 g of ethylhexyl thioglycolate Example 16

A mixture of 744 g of water, 0.25 g of sodium lauryl sulfate and 70g of feedstream 1 is heated to 40° C. Then 16 g of a 7% strength aqueous sodium persulfate solution are added. The mixture is subsequently heated to 80° C., and the remainder of feedstream 1 is metered in over the course of two hours. Then 178 g of water are added and the mixture is afterpolymerized at 80° C. for two hours.
Feedstream 1:

300 g of water 2 g of sodium lauryl sulfate 15.7 g of PEO (20)-sorbitan monooleate 422 g of tert-butyl acrylate 63 g of ethyl acrylate 145 g of methacrylic acid 3 g of ethylhexyl thioglycolate 70 g of silicone copolyol (Silwet™ L7605)

Example 17

A mixture of 744 g of water, 0.25 g of sodium lauryl sulfate and 70 g of feedstream 1 is heated to 40° C. Then 16 g of a 7% strength aqueous sodium persulfate solution are added. The mixture is subsequently heated to 80° C., and the remainder of feedstream 1 is metered in over the course of two hours. Then 178 g of water are added and the mixture is afterpolymerized at 80° C. for two hours.
Feedstream 1:

300 g of water 2 g of sodium lauryl sulfate 15.7 g of silicone copolyol (Silwet™ L7600)

470 g of tert-butyl acrylate 70 g of ethyl acrylate 161 g of methacrylic acid 3 g of ethylhexyl thioglycolate Example 18

A mixture of 744 g of water, 0.25 g of sodium lauryl sulfate and 70 g of feedstream 1 is heated to 40° C. Then 16 g of a 7% strength aqueous sodium persulfate solution are added. The mixture is subsequently heated to 80° C., and the remainder of feedstream 1 is metered in over the course of two hours. Then 178 g of water are added and the mixture is afterpolymerized at 80° C. for two hours.
Feedstream 1:

300 g of water 2 g of sodium lauryl sulfate 15.7 g of PEO (20)-sorbitan monooleate (Tween 80)

422 g of tert-butyl acrylate 63 g of ethyl acrylate 145 g of methacrylic acid 3 g of ethylhexyl thioglycolate 70 g of silicone copolyol (Silwe™ L7600)

Example 19

Comparative Example

A mixture of 744 g of water, 0.25 g of sodium lauryl sulfate and 70 g of feedstream 1 is heated to 40° C. Then 16 g of a 7% strength aqueous sodium persulfate solution are added. The mixture is subsequently heated to 80° C., and the remainder of feedstream 1 is metered in over the course of two hours. Then 178 g of water are added and the mixture is afterpolymerized at 80° C. for two hours.
Feedstream 1:

300 g of water 2 g of sodium lauryl sulfate 15.7 g of PEO (20)-sorbitan monooleate (Tween 80)

470 g of tert-butyl acrylate 70 g of ethyl acrylate 161 g of methacrylic acid 3 g of ethylhexyl thioglycolate Example 20

A mixture of 100 g of vinylcaprolactam, 100 g of ethanol, 100 g of dimethicone copolyol (Wacker Belsil™ DMC 6031) and 0.75 g of t-butyl perpivalate is heated to 70° C. in a closed reactor flushed with nitrogen. Then feedstream 1 is metered in over the course of 3 h and feedstream 2 over the course of 4 h. After the end of feedstream 1, afterpolymerization is conducted for 1 h. Then feedstream 3 is added and the mixture is heated to 130° C. under superatmospheric pressure. Afterpolymerization is conducted at 130° C. for 10 h, and then the batch is cooled.

Feedstream 1:
 800 g of vinylcaprolactam
 347 g of ethanol
Feedstream 2:
 1.5 g of t-butyl perpivalate
 100 g of ethanol
Feedstream 3:
 5 g of di-t-butyl peroxide
 187 g of ethanol

Example 21

A mixture of 100 g of vinylcaprolactam, 100 g of ethanol, 100 g of dimethicone copolyol (Wacker Belsil™ DMC 6032) and 0.75 g of t-butyl perpivalate is heated to 70° C. in a closed reactor flushed with nitrogen. Then feedstream 1 is metered in over the course of 3 h and feedstream 2 over the course of 4 h. After the end of feedstream 1, afterpolymerization is conducted for 1 h. Then feedstream 3 is added and the mixture is heated to 130° C. under superatmospheric pressure. Afterpolymerization is conducted at 130° C. for 10 h, and then the batch is cooled.

Feedstream 1:
 800 g of vinylcaprolactam
 347 g of ethanol
Feedstream 2:
 1.5 g of t-butyl perpivalate
 100 g of ethanol
Feedstream 3:
 5 g of di-t-butyl peroxide
 187 g of ethanol

Example 22

Comparative Example

A mixture of 100 g of vinylcaprolactam, 100 g of ethanol and 0.75 g of t-butyl perpivalate is heated to 70° C. in a closed reactor flushed with nitrogen. Then feedstream 1 is metered in over the course of 3 h and feedstream 2 over the course of 4 h. After the end of feedstream 1, afterpolymerization is conducted for 1 h. Then feedstream 3 is added and the mixture is heated to 130° C. under superatmospheric pressure. Afterpolymerization is conducted at 130° C. for 10 h, and then the batch is cooled.

Feedstream 1:
 800 g of vinylcaprolactam
 347 g of ethanol
Feedstream 2:
 1.5 g of t-butyl perpivalate
 100 g of ethanol
Feedstream 3:
 5 g of di-t-butyl peroxide
 187 g of ethanol

Example 23

The polymer solution from Example 22 was blended, after polymerization, with 10% by weight of a silicone surfactant (Wacker Belsil™ DMC 6032).

Films of the polymers from the examples were produced on glass plates by knife-coating solutions or dispersions of the polymers. The transparency, surface roughness and frictional properties of these polymer films are measured (see Table 1).

It is found that all films according to the invention are transparent and have a particularly smooth surface with a low friction resistance.

Films of Comparison Example 7 are likewise transparent but have a rougher surface and, in particular, a very much higher friction resistance. The same poor frictional behavior is found with films from Examples 8, 14, 19, 22 and 23. Films prepared analogously from the blends of Examples 8 and 23 have an extremely high tack. The films are very soft and therefore unsuitable for use as film formers.

Tests of polymers 1–23 for their suitability as hair treatment compositions give similar results (Table 1). For these tests, locks of hair were sprayed with a defined amount of a standard formulation (2% by weight of polymer, 40% of dimethyl ether, 58% of ethanol). After the locks of hair have been dried, the combability and handle of the strands of hair is assessed. The polymers according to the invention prepared in the presence of silicone surfactants result in a much better handle of the treated hair strands than strands of hair treated with the comparative polymers 7, 14, 19 and 22.

TABLE 1

| Example | Film smoothness | Transparency | Combability | Handle |
|---|---|---|---|---|
| 1 | o | + | o | o |
| 2 | + | + | + | − |
| 3 | + | + | + | o |
| 4 | + | + | + | o |
| 5 | ++ | + | ++ | ++ |
| 6 | + | + | ++ | o |
| 7 | −− | + | − | −− |
| 8 | −− | o | −* | −* |
| 12 | + | + | ++ | ++ |
| 13a | + | + | ++ | + |
| 13b | + | + | ++ | + |
| 14 | − | + | ++ | o |
| 20 | + | + | + | + |
| 21 | + | + | ++ | + |
| 22 | − | + | o | − |
| 23 | −− | − | −* | −* |

*because of the greatly excessive tack, no hair lock test was carried out
The entries in the above table have the following meanings:
++ = very good performance
+ = good performance
o = satisfactory performance
− = not satisfactory
−− = inadequate

We claim:

1. A water-soluble or water-dispersible polymer which is obtained by subjecting (a) ethylenically unsaturated monomers to free-radical polymerization in the presence of (b) polyalkylene oxide-containing silicone derivatives of the formula I

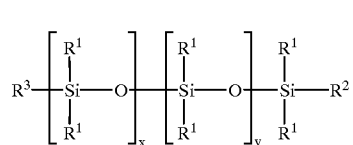

(I)

where:

$R^2 = CH_3$ or 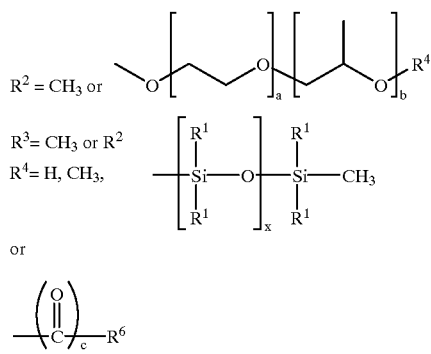

$R^3 = CH_3$ or $R^2$ $R^4 = H, CH_3,$ or

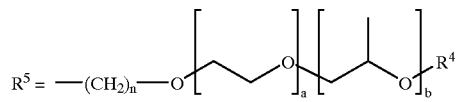

$R^6$ is an organic radical of 1 to 40 carbons which may contain amino, carboxyl or sulfonate groups, or, if c=0, is the anion of an inorganic acid, and where the radicals $R^1$ can be identical or different and alternatively derive from the group of aliphatic hydrocarbons of 1 to 20 carbons, are cyclic aliphatic hydrocarbons of 3 to 20 carbons, are aromatic in nature or are $R^5$, where:

$R^5 =$ 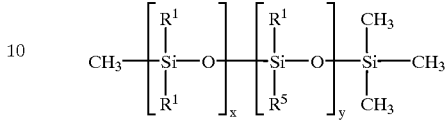

with the proviso that at least one of the radicals $R^1$, $R^2$ or $R^3$ is a polyalkylene
oxide-containing radical as defined above,
and n is an integer from 1 to 6, x and y are integers such that the molecular weight of the polysiloxane block is from 300 to 30,000, a, b can be integers from 0 to 50 with the proviso that the sum of a and b is greater than 0, and c is 0 or 1.

2. The water-soluble or water-dispersible polymer as claimed in claim 1, wherein formula I is:

$$CH_3 \!-\!\!\left[\begin{array}{c}R^1\\|\\Si\!-\!O\\|\\R^1\end{array}\right]_x\!\!\left[\begin{array}{c}R^1\\|\\Si\!-\!O\\|\\R^5\end{array}\right]_y\!\!\begin{array}{c}CH_3\\|\\Si\!-\!CH_3\\|\\CH_3\end{array}$$

where $R^1$, x and y are as defined in claim 1.

3. The water-soluble or water-dispersible polymer as claimed in claim 1, wherein the proportions are (a) 50–99.9% by weight and (b) 0.1–50% by weight.

4. A haircare composition containing the water-soluble or water-dispersible polymer as claimed in claim 1.

5. A cosmetic composition, which comprises at least one water soluble or dispersible polymer as claimed in claim 1.

6. hair cosmetic selected from the group consisting of setting polymers in hairsprays, setting foams, hair mousse, hair gel and shampoos, which comprises at least one water soluble or dispersible polymer as claimed in claim 1.

7. An auxiliary for hair cosmetics selected from the group consisting of setting polymers in hairsprays, setting foams, hair mousse, hair gel and shampoos, which comprises at least one water soluble or dispersible polymer as claimed in claim 1.

* * * * *

UNITED STATES PATENT AND TRADEMARK OFFICE
CERTIFICATE OF CORRECTION

PATENT NO. : 6,403,074 B1
DATED : June 11, 2002
INVENTOR(S) : Blankenburg et al.

It is certified that error appears in the above-identified patent and that said Letters Patent is hereby corrected as shown below:

Column 16,
Line 25, insert -- A -- before "hair".

Signed and Sealed this

Twenty-third Day of July, 2002

Attest:

Attesting Officer

JAMES E. ROGAN
Director of the United States Patent and Trademark Office